United States Patent [19]

Robin et al.

[11] Patent Number: 5,386,016

[45] Date of Patent: Jan. 31, 1995

[54] 2″,3″,4′-TRI(ACETYL)-4″,6″-ETHYLIDINE-β-D-GLUCOPYRANOSIDES, THEIR PREPARATION AND THEIR USE FOR THE PREPARATION OF 4′-DEMETHYLEPIPODOPHYLIOTOXING ETHYLIDENE-β-D-GLUCOPYRANOSIDE

[75] Inventors: Jean-Pierre Robin; Valerie Lenain, both of LeMans, France

[73] Assignee: Pierre Fabre Medicament, France

[21] Appl. No.: 156,863

[22] Filed: Nov. 19, 1993

Related U.S. Application Data

[63] Continuation of Ser. No. 2,098, Jan. 8, 1993, abandoned, which is a continuation of Ser. No. 661,853, Feb. 27, 1991, abandoned.

[30] Foreign Application Priority Data

Feb. 27, 1990 [FR] France .................. 90 02408

[51] Int. Cl.$^6$ .............................. C07H 15/24
[52] U.S. Cl. ........................ 536/18.1; 536/4.1; 536/18.5; 536/18.6; 536/115; 536/120
[58] Field of Search ............ 536/4.1, 18.1, 18.2, 536/18.4, 18.5; 549/448

[56] References Cited

U.S. PATENT DOCUMENTS

| | | | |
|---|---|---|---|
| 3,524,844 | 8/1970 | Keller-Juslen et al. | 536/18.1 |
| 4,359,572 | 11/1982 | Umezawa et al. | 536/13.8 |
| 4,564,675 | 1/1986 | Kurabayashi et al. | 536/18.1 |
| 4,757,138 | 7/1988 | Fujii et al. | 536/18.1 |
| 4,824,943 | 4/1989 | Horii et al. | 536/18.1 |
| 4,900,814 | 2/1990 | Sterling et al. | 536/18.5 |
| 4,935,504 | 6/1990 | Saulnier et al. | 536/18.1 |
| 4,962,146 | 10/1990 | Mallams et al. | 514/30 |

FOREIGN PATENT DOCUMENTS

| | | |
|---|---|---|
| 0043966 | 1/1982 | European Pat. Off. |
| 0415453 | 3/1991 | European Pat. Off. |
| 61-134396 | 6/1986 | Japan |
| 86/00018 | 1/1986 | WIPO |

OTHER PUBLICATIONS

McOmie; Protective Groups in Organic Chemistry, pp. 109–118 (1973).
Fock; Chemical Abstracts 96:164565w (1982).

*Primary Examiner*—John W. Rollins
*Assistant Examiner*—Howard C. Lee
*Attorney, Agent, or Firm*—Dressler, Goldsmith, Shore, Milnamow, Ltd.

[57] ABSTRACT

The invention relates to 2″,3″,4′-tris(acetyl)-4″,6″-ethylidene-β-D-glucopyranosides, their preparation and their use for the preparation of 4′-demethylepipodophyllotoxin ethylidene-β-D-glucopyranoside. The compounds of the invention are of the formula Their process of preparation comprises the following stages:

acylation of a glycosyl derivative acylation of an aglycone coupling of the acylated glycosyl derivative and the acylated aglycone, in the presence of a Lewis acid, the acylation being carried out using an acid chloride, which is optionally identical for the two stages of acylation, in which the carbon in α of the carbonyl function bears at least one heteroatom chosen from among O and S.

8 Claims, No Drawings

2",3",4'-TRI(ACETYL)-4",6"-ETHYLIDINE-β-D-GLUCOPYRANOSIDES, THEIR PREPARATION AND THEIR USE FOR THE PREPARATION OF 4'-DEMETHYLEPIPODOPHYLIOTOXING ETHYLIDENE-β-D-GLUCOPYRANOSIDE

This application is a continuation of application Ser. No. 08/002,098, filed Jan. 8, 1993, abandoned which is a continuation of application Ser. No. 07/661,853, filed Feb. 27, 1991, abandoned.

The present invention relates to 4'-demethylepipodophyllotoxin 2",3",4'-tris(acetyl)-4",6"-ethylidene-β-D-glucopyranosides which are useful for the preparation of 4'-demethylepipodophyllotoxin ethylidene-β-D-glucopyranoside which is known as a medicament, a process for their preparation from esters of glycosyl and aglycone derivatives, as well as the esters of the glycosyl and aglycone derivatives used.

4'-Demethylepipodophyllotoxin ethylideneglucoside is known to be an active principle of major interest in human anticancer therapy. This compound is of the formula 1'

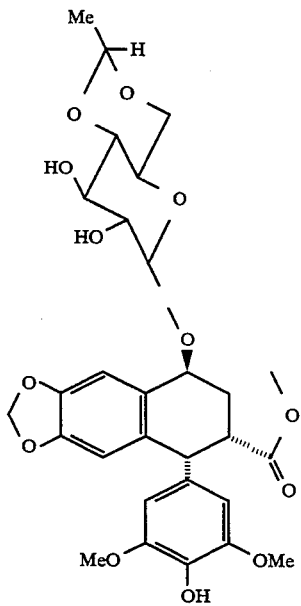

Various processes for the preparation of this compound are known. They consist, in general, of coupling a glycosyl intermediate whose hydroxyls in position 4 and 6 are blocked in the form of a cyclic acetal and the hydroxyls in position 2 and 3 are protected, with an aglycone whose hydroxyl in 4' is also protected, then of carrying out the deprotection of the compound obtained by the coupling reaction.

The glycosyl intermediate is represented by the formula 2

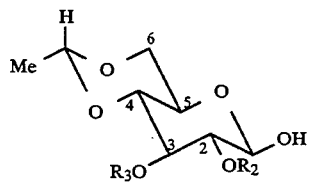

in which $R_2$ and $R_3$ represent the protecting groups of the hydroxyls in position 2 and 3.

The aglycone is represented by the formula 3

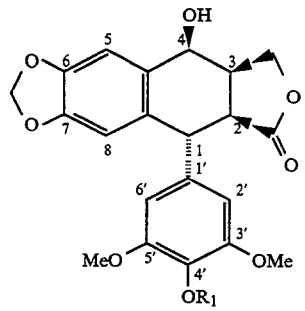

in which $R_1$ represents the protecting group of the hydroxyl in position 4'.

The compound resulting from the coupling of a compound 2 with a compound 3 is represented by the formula 1

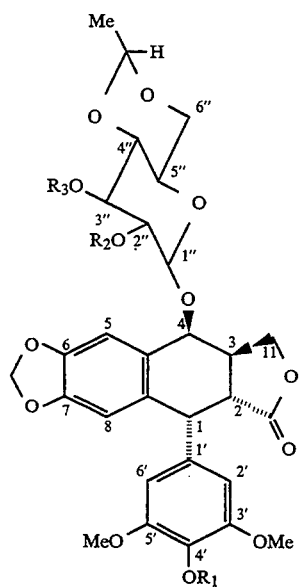

A first synthesis route, described in the literature, employs acetates to protect the glycosyl intermediate and a benzyloxycarbonyl for the aglycone. In the compound 1 obtained, $R_2=R_3=Ac$, $R_1=CO_2Bn$ [M. Kuhn, and A. Von Wartburg, Helv. Chim. Acta, 52, 948–955 (1969)]. It has two disadvantages: a) the need for two successive unblocking steps for each type of protecting group, b) too high a stability of the acetic esters, requiring prolonged reaction times, leading to a proportion of secondary products which is unacceptable to the deblocking (anomerization and opening of the lactone ring by transesterification).

A second route described employs the same glycosyl intermediate, but with formates in lieu and place of acetates. In the compound 1 obtained, $R_2=R_3=CHO$, $R_1=CO_2Bn$ [M. Kuhn, C. Keller-Juslen, J. Renz and A. Von Wartburg, (Sandoz Ltd) CH-518927 (Cl.CO7d), Dec. 15, 1971, 2845/68, Feb. 27, 1968]. This method also has the disadvantage of requiring a special unblocking of the carbonate situated in 4'. Moreover, contrary to the acetic esters of the first route, these formic esters are so labile that they do not permit conservation of the glycosyl intermediates, which is a disadvantage during the use of the process on an industrial scale.

A third route, described more recently [JP 58,219,196 (83,219,196; JP 58,225,096 (83,225,096); EP 111,058; JP 101,766; EP 196,618; JP 61,122,294 (86,122,294); JP 61,103,883 (86,103,883)] employs compounds of the type 1, but containing α-haloacetates for protecting the hydroxyls in 2 and 3 of the glycosyl part and β-haloalkoxycarbonates for protecting the hydroxyl in 4′ of the aglycone, in other words: $R_1=CX_mH_nCH_2OCO—$, $R_2=R_3=CX_mH_nCO—$, with $m+n=3$ and $X=F$, Cl, Br or I) or again α-haloacetates for protecting the three sites, in other words: $R_1=R_2=R_3=CX_mH_nCO—$, with $m+n=3$ and $X=F$, Cl, Br or I. This method has the disadvantage, during deprotection by hydrogenolysis, of employing glycosyl intermediates with too weak a difference in reactivity in 2 and 3 in relation to the benzyloxycarbonyl protecting group of the anomeric hydroxyl, in position 1. Moreover, the presence of esters of strong organic acids protecting the hydroxyl adjacent to the hemiacetal hydroxyl leads, due to the anomeric effect, to an isomerization which is more difficult to control. The poor stability resulting therefrom does not allow, moreover, a prolonged storage of the glycosyl intermediates in the desired anomeric form (beta), which is a major disadvantage in respect of the therapeutic use of the final product. Furthermore, the analytical control of the anomeric purity of the glycosyl intermediates 2, in which $R_2=R_3=CX_mH_nCO—$, $CX_mH_nCH_2OCO—$ with $m+n=3$, $X=F$, Cl, Br or I, is more difficult to carry out because these intermediates do not contain a chromophore which absorbs ultraviolet light. Moreover, this process has the disadvantage of requiring sophisticated conditions for the selective blocking of the phenol hydroxyl of the aglycone (low temperature), because of the high reactivity of the acylating agents used with respect to the two types of sites. Finally, the majority of the groups described are very unstable (iodoacetate, bromoacetate, trifluoroacetate) and do not permit the intermediates to be isolated.

The aim of the present invention is to eliminate these disadvantages, that is to say to minimize the formation of undesirable products during the deprotection of the compound 1 to obtain the compound 1′, to increase the stability and the purity of the glycosyl intermediates 2, to facilitate the analytical control of the purity of the intermediates, and to permit the deprotection of the compound 1 in a single step.

This aim is achieved by a process for the preparation of the compounds 1 employing special reagents for protecting the hydroxyls in position 2 and 3 of the glycosyl intermediates 2 on the one hand, the hydroxyl in position 4′ of the aglycone 3 on the other.

The present invention relates to a process for the preparation of 4′-demethylepipodophyllotoxin 2″,3″,4′-tris(acetyl)-4″,6″-ethylidene-β-D-glucopyranosides 1, and the compounds 1 obtained.

The invention also relates to the glycosyl intermediates 2 and the aglycones 3 obtained as synthesis intermediates during the implementation of the process of the invention.

Finally, the invention relates to the application of the compounds 1 to the preparation of 4′-demethylepipodophyllotoxin ethylideneglucoside.

According to the invention, the process for the preparation of compounds of the formula 1

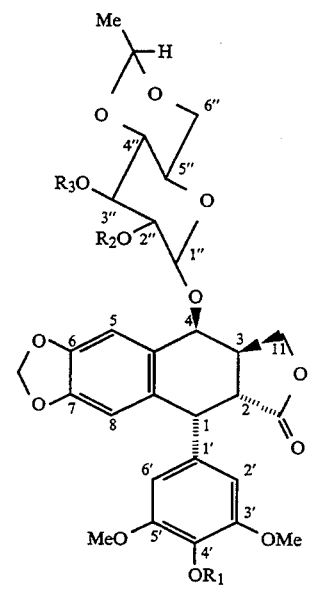

in which $R_1$, $R_2$ and $R_3$, which may be identical or different, represent acyl radicals in which the carbon in α of the carbonyl function bears at least one heteroatom chosen from among O and S, comprises the following stages:

1) The preparation of a glycosyl derivative of the formula 2

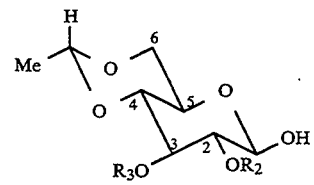

in which $R_2$ and $R_3$ have the meaning given above, by reacting at least one acid chloride $R_2Cl$ and/or $R_3Cl$ in which the carbon in α of the carbonyl function bears at least one heteroatom chosen from among O and S with a glycosyl derivative of the formula 2′,

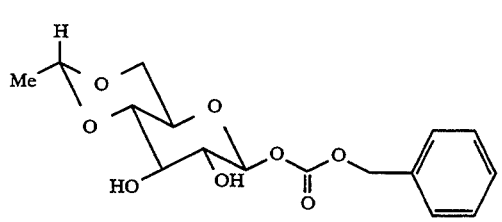

followed by hydrogenolysis catalyzed by palladized carbon.

2) The preparation of an aglycone of the formula 3,

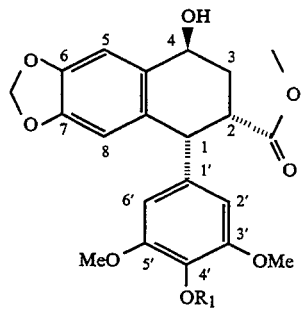

(3)

in which $R_1$ has the meaning given above, by reacting 4'-demethylepipodophyllotoxin 3'

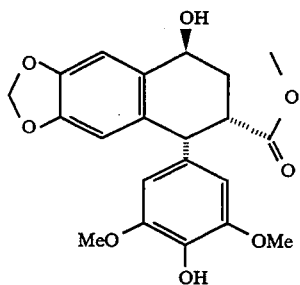

(3')

with an acid chloride $R_1Cl$ in which the carbon in α of the carbonyl function bears at least one heteroatom chosen from among O and S, the reaction being carried out in a neutral medium; the order in which the stages 1) and 2) are carried out being unimportant.

3) The coupling of a glycosyl derivative 2 with an aglycone 3, in the presence of a Lewis acid in solution in a chlorine-containing hydrocarbon.

The acid chlorides $R_1Cl$, $R_2Cl$ and $R_3Cl$ used in the stages 1 and 2 may be identical or different. Preferably, the acylation of the compound 2' is carried out by a single acid chloride, that is to say $R_2=R_3$.

Among suitable $R_1$, $R_2$ or $R_3$ acyl radicals, those of formulae 4a to 4h below may be mentioned

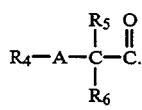

(4a)

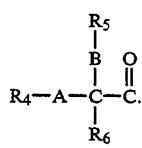

(4b)

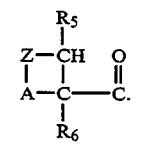

(4c)

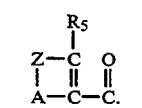

(4d)

-continued

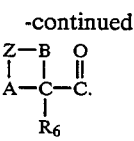

(4e)

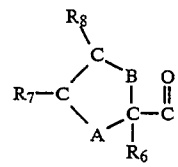

(4f)

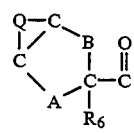

(4g)

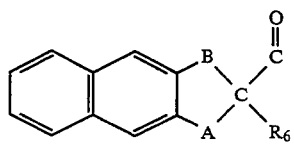

(4h)

in which

A and B, which may be identical or different, each represent a divalent heteroatom of oxygen and/or sulfur, $R_4$, $R_5$, $R_6$, $R_7$ and $R_8$, which may be identical or different, each represent either a hydrogen atom or an alkyl radical with 1 to 8 carbon atoms which is saturated, monounsaturated or polyunsaturated, linear or branched, or an alkyl radical chosen from among the following groups: Ar—$(CH_2)_n$— (where n is an integer equal to 1 or 2, and Ar is a benzene, a naphthalene or an anthracene), $Ar_2$-CH— (where Ar is a benzene or a naphthalene), or an aromatic ring chosen from among the groups of the formulae 5a to 5c below

(5a)

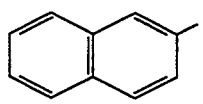

(5b)

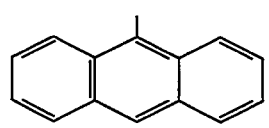

(5c)

where Σ represents a set of 1 to 4 identical or different substituents chosen from among the following groups or atoms: OMe, OEt, F, Cl, Br, I and NO2.

Z and Q which may be identical or different, each represent a divalent group, which may be chosen from among —$(CH_2)_n$—, —$CH(CH_3)$—$CH_2$—, —$CH_2$—$CH(CH_3)$—, —$CH(CH_3)$—$CH(CH_3)$—, —$CH(C_2H_5)$—$CH_2$—, —$CH_2$—$CH(C_2H_5)$—, —CH=CH—, —CH=C($CH_3$)—, —C($CH_3$)=CH—, —CH=CH—$(CH_2)_m$ and —CH=CH—CH=CH—, n being an integer from 1 to 4 inclusive and m an integer equal to 1 or 2, a 1,2-phenylene, 2,3-naphthylene or 2,3-anthrylene radical or a tetravalent group of the following formula:

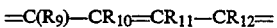

where $R_9$, $R_{10}$, $R_{11}$ and $R_{12}$ are alkyl radicals having from 1 to 6 carbon atoms or heteroatoms of oxygen, sulfur, halogens (F, Cl, Br, I), or nitrogen. These acyl radicals comprise in particular the alkoxyacetyls

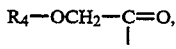

for example those for which $R_4$ is a methyl, ethyl, benzyl or menthyl.

The acyl radicals also comprise the aryloxyacetyls

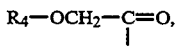

for example those for which $R_4$ is a phenyl, naphthyl, anthryl or phenanthryl ring, these rings optionally bearing from 1 to 4 substituents chosen from among OMe, OEt, F, Cl, Br, I and $NO_2$.

Among the acyl radicals are also included the thioalkylacetyls

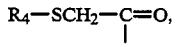

for which $R_4$ may be in particular a methyl or benzyl.

Other acyl radicals are the thioarylacetyls $R_4$—S—$CH_2$—C=O, in which $R_4$ may be in particular a phenyl, naphthyl, anthryl or phenanthryl.

Another group of suitable acyl radicals comprises the 2,2-dioxtacetylarylenes

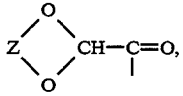

in which Z represents for example a 1,2-phenylene radical, a 2,3-naphthylene radical or a 2,3-anthrylene radical. Another group of suitable acyl radicals comprises the 2-furoyl or 2-thenoyl radicals.

For the first stage of the process according to the invention, the compound 2' is reacted with the appropriate acid chloride in a haloalkyl solvent and an intermediate compound of the formula 6 is obtained

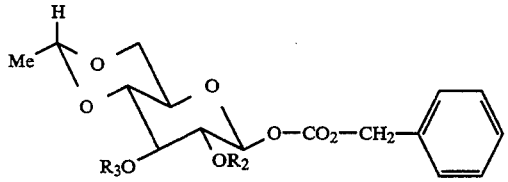

in which $R_2$ and $R_3$ have the meaning given previously. Then hydrolysis of the 1-benzyloxycarbonyl group of the compound 6 is carried out in the presence of molecular hydrogen, using palladized carbon as catalyst. This hydrogenolysis is carried out under atmospheric pressure, at a temperature between $-10°$ C. and $0°$ C., in a ketone solvent.

The haloalkyl solvent may be chosen from among dichloromethane, dichloroethane and chloroform. The ketone solvent may be chosen from among acetone, methyl ethyl ketone or methyl isobutyl ketone. The intermediate compound obtained may be isolated and purified before hydrogenolysis. It may also be used in the crude state for hydrogenolysis. The product obtained after hydrogenolysis is a glycosyl derivative of the formula 2 in which the radicals $R_2$ and $R_3$ have the meaning given previously.

For the second stage of the process according to the invention, 4'-demethylepipodophyllotoxin 3' is reacted with an acid chloride such as is defined previously. The reaction is carried out in a neutral medium. The acid chloride is added sufficiently slowly in order to constantly be in low concentration relative to the compound 3', so as to limit the reaction of the acid chloride with the hydroxyl in position 4 of the compound 3'. The progress of the reaction is monitored by controlling the temperature of the reaction medium and by thin layer chromatography. The aglycones 3 obtained possess an excellent crystallogenic capacity, which makes their purification easy. They are of the formula 3 in which $R_1$ has the meaning given previously.

For the third stage of the process according to the invention, the reaction temperature is maintained between $-25°$ C. and $-20°$ C., in order to limit the formation of the undesirable $\alpha$ anomer. The chlorine-containing hydrocarbon is advantageously chosen from among dichloromethane or dichloroethane.

The compounds 1 thus obtained are useful for the preparation of 4'-demethylepipodophyllotoxin 4'',6''-ethylidene-$\beta$-D-glucopyranoside 1'. The process for the preparation of 1' consists of carrying out a transesterification of the compound 1 with an alcohol of low boiling point, in the presence of a transesterification catalyst. The reaction is carried out in a co-solvent—of the compound 1 and of the said alcohol—, for example tetrahydrofuran. A suitable alcohol is methanol. The reaction mixture is brought to the solvent reflux temperature for a period of between 1 and 2 hours.

The groups removed from the compound 1 form, with the alcohol used, an ester which is separated with the other minor impurities during the final operation of purification by chromatography.

The present invention is explained in more detail by the examples hereinafter, which are given by way of illustration with no limitation being implied.

Examples 1 to 20 illustrate the preparation of various glycosyl derivatives of the formula 2.

EXAMPLE 1

2,3-Bis(2-phenoxyacetyl)-4,6-ethylidene-$\beta$-D-glucose 2a

Into a mixture of dry dichloromethane (25 l) and pyridine (1.41 l), 1-benzyloxycarbonyl-4,6-ethylidene-$\beta$-D-glucose (2.5 kg, that is to say 7.35 moles) was introduced with stirring and the reaction mixture was cooled to $0°$ C. 2-Phenoxyacetyl chloride (2.45 l, that is to say 17.64 moles) was added and the reaction pursued for 1 h 30 at $20°$ C. After monitoring by thin layer chromatography, water was added, and the organic phase was washed with a sodium bicarbonate solution, dried over $MgSO_4$, then evaporated under reduced pressure. The oil obtained was mixed with hot methanol (7 l) and 2.7 kg of the 1-benzyloxycarbonyl-2,3-bis(2-phenoxyacetyl)-4,6-ethylidene-β-D-glucose intermediate 6a was obtained (yield=60%). A sample was recrystallized. Its structural analysis gave the following results: m.p.=128°-130° C.; $[\alpha]_D^{22}=-18°$(c=1; CHCl$_3$); IR (Nujol) (ν max); 1769 (C=O), 1600, 1377 and 1198; $^1$H NMR 400 MHz (CDCl$_3$) (δ ppm): 7.34 (5H, m, arom. H); 7.21 (5H, m, arom. H); 6.92 (2H, m, arom. H); 6.84 and 6.80 (4H, 2d, J=7.9 Hz, arom. H); 5.63 (1H, d, $J_{1''\text{-}2''}$=8.1 Hz, H-1''$_{(ax)}$); 5.35 (1H, t, $J_{3''\text{-}2'',4''}$=9 Hz, H-3''); 5.18 (1H, H-3''); 5.17 and 5.14 (2H, 2d, $J_{AB}$=12.0 Hz, CH$_2$-OCO); 4.64 (1H, q, $JT_{7''\text{-}8''}$=5.0 Hz, H-7''); 4.59 and 4.54 (2H, 2d, $J_{AB}$=16.5 Hz, CH$_2$-O); 4.52 and 4.46 (2H, 2d, $J_{AB}$=16.5 Hz, CH$_2$-O); 4.22 (1H, m, H-6''$_{(A)}$); 3.52 (3H, m, H-6''$_{(B)}$, H-4'' and H-5'') and 1.30 (3H, d, $J_{8''\text{-}7''}$=5 Hz, H-8'').

10% Palladized carbon (125 g) and the crude 1-benzyloxycarbonyl-2,3-bis(2-phenoxyacetyl)-4,6-ethylidene-β-D-glucose above (1.73 kg, that is to say 2.85 moles) were introduced into dry acetone (9.5 l). The mixture was vigorously stirred and cooled to −5° C. After dissolution, hydrogen was absorbed at atmospheric pressure for 1 h. The reaction mixture was next filtered, then evaporated under reduced pressure at 30°-35° C. The 2,3-bis(2-phenoxyacetyl)-4,6-ethylidene-β-D-glucose 2a was obtained in the form of a colorless oil, stored at −15° C. The yield is 48%.

A sample was recrystallized; its analytical study gave the following results: m.p.=66°-70° C.; $[\alpha]_D^{22}=-1°$(c=1, CHCl$_3$); IR (CHCl$_3$) (ν max): 1776 (C=O), 1609 and 1497 cm$^{-1}$.

EXAMPLE 2

2,3-Bis (2-naphthoxyacetyl)-4,6-ethylidene-β-D-glucose 2b.

The procedure in Example 1 was repeated, but using 2-naphthoxyacetyl chloride as a substitute for 2-phenoxyacetyl chloride, and for a reaction time of 8 h, in order to obtain the intermediate 6b. This intermediate 6h was directly hydrogenolyzed in the crude state to give the product 2b in the form of a colorless oil, with a total yield of 29%. The product 2b was stored in its original state at −15° C.

EXAMPLE 3

2,3-Bis[2-(2-methoxyphenoxy)acetyl]-4,6-ethylidene-β-D-glucose 2c.

The procedure in Example 1 is repeated, but using 2-(2-methoxyphenoxy)acetyl chloride as a substitute for 2-phenoxyacetyl chloride, and for a reaction time of 3 h, in order to obtain the intermediate 6c. This intermediate 6c was directly hydrogenolyzed in the crude state to give the product 2c in the form of a colorless oil, with a total yield of 49%. The product 2c was stored in its original state at −15° C.

EXAMPLE 4

2,3-Bis[2-(4-methoxyphenoxy)acetyl]-4,6-ethylidene-β-D-glucose 2d.

The procedure in Example 1 is repeated, but using 2-(4-methoxyphenoxy)acetyl chloride as a substitute for 2-phenoxyacetyl chloride, and for a reaction time of 4 h, in order to obtain the intermediate 6d. This intermediate 6d was directly hydrogenolyzed in the crude state to give the product 2d in the form of a colorless oil, with a total yield of 37%. The product 2d was stored in its original state at −15° C.

EXAMPLE 5

2,3-Bis[2-(2-nitrophenoxy)acetyl]-4,6-ethylidene-β-D-glucose 2e.

The procedure in Example 1 is repeated, but using 2-(2-nitrophenoxy)acetyl chloride as a substitute for 2-phenoxyacetyl chloride, and for a reaction time of 8 h, in order to obtain the intermediate 6e. This intermediate 6e was directly hydrogenolyzed in the crude state to give the product 2e in the form of a colorless oil, with a total yield of 38%. The product 2e was stored in its original state at −15° C.

EXAMPLE 6

2,3-Bis[2-(4-nitrophenoxy)acetyl]-4,6-ethylidene-β-D-glucose 2f.

The procedure in Example 1 is repeated, but using 2-(4-nitrophenoxy)acetyl chloride as a substitute for 2-phenoxyacetyl chloride, and for a reaction time of 8 h, in order to obtain the intermediate 6f. This intermediate 6f was directly hydrogenolyzed in the crude state to give the product 2f in the form of a colorless oil, with a total yield of 40%. The product 2f was stored in its original state at −15° C.

EXAMPLE 7

2,3-Bis[2-(4-chlorophenol)acetyl]-4,6-ethylidene-β-D-glucose 2g.

The procedure in Example 1 is repeated, but using 2-(4-chlorophenoxy)acetyl chloride as a substitute for 2-phenoxyacetyl chloride, and for a reaction time of 8 h, in order to obtain the intermediate 6g. This intermediate 6g was directly hydrogenolyzed in the crude state to give the product 2g in the form of a colorless oil, with a total yield of 31%. The product 2g was stored in its original state at −15° C.

EXAMPLE 8

2,3-Bis[2-(2,4-dichlorophenoxy)acetyl]-4,6-ethylidene-62 -D-glucose 2h.

The procedure in Example 1 is repeated, but using 2-(2,4-dichlorophenoxy)acetyl chloride as a substitute for 2-phenoxyacetyl chloride, and for a reaction time of 8 h, in order to obtain the intermediate 6h. This intermediate 6h was directly hydrogenolyzed in the crude state to give the product 2h in the form of a colorless oil, with a total yield of 46%. The product 2h was stored in its original state at −15° C.

EXAMPLE 9

2,3-Bis[2-(2,4,5-trichlorophenoxy)acetyl]-4,6-ethylidene-β-D-glucose 2i.

The procedure in Example 1 is repeated, but using 2-(2,4,5-trichlorophenoxy)acetyl chloride as a substitute for 2-phenoxyacetyl chloride, and for a reaction time of 10 h, in order to obtain the intermediate 6i. This intermediate 6i was directly hydrogenolyzed in the crude state to give the product 2i in the form of a colorless oil, with a total yield of 18%. The product 2i was stored in its original state at −15° C.

EXAMPLE 10

2,3-Bis[2-(2,4,6-trichlorophenoxy)acetyl]-4,6-ethylidene-β-D-glucose 2j.

The procedure in Example 1 is repeated, but using 2-(2,4,6-trichlorophenoxy)acetyl chloride as a substitute for 2-phenoxyacetyl chloride, and for a reaction time of 11 h, in order to obtain the intermediate 6j. This intermediate 6j was directly hydrogenolyzed in the crude state to give the product 2j in the form of a colorless oil, with a total yield of 26%. The product 2j was stored in its original state at −15° C.

EXAMPLE 11

2,3-Bis[2-(2-fluorophenoxy)acetyl]-4,6-ethylidene-β-D-glucose 2k.

The procedure in Example 1 is repeated, but using 2-(2-fluorophenoxy)acetyl chloride as a substitute for 2-phenoxyacetyl chloride, and for a reaction time of 5 h, in order to obtain the intermediate 6k. This intermediate 6k was directly hydrogenolyzed in the crude state to give the product 2k in the form of a colorless oil, with a total yield of 32%. The product 2k was stored in its original state at −15° C.

EXAMPLE 12

2,3-Bis(2-methoxyacetyl)-4,6-ethylidene-β-D-glucose 2l.

The procedure in Example 1 is repeated, but using 2-methoxyacetyl chloride as a substitute for 2-phenoxyacetyl chloride, and for a reaction time of 5 h, in order to obtain the intermediate 6l. This intermediate 6l was directly hydrogenolyzed in the crude state to give the product 2l in the form of a colorless oil, with a total yield of 41%. The product 2l was stored in its original state at −15° C.

EXAMPLE 13

2,3-Bis (2-ethoxyacetyl)-4,6-ethylidene-β-D-glucose 2m.

The procedure in Example 1 is repeated, but using 2-ethoxyacetyl chloride as a substitute for 2-phenoxyacetyl chloride, and for a reaction time of 7 h, in order to obtain the intermediate 6m. This intermediate 6m was directly hydrogenolyzed in the crude state to give the product 2m in the form of a colorless oil, with a total yield of 35%. The product 2m was stored in its original state at −15 ° C.

EXAMPLE 14

2,3-Bis(2-benzoxyacetyl)-4,6-ethylidene-β-D-glucose 2n.

The procedure in Example 1 is repeated, but using 2-benzoxyacetyl chloride as a substitute for 2-phenoxyacetyl chloride, and for a reaction time of 8 h, in order to obtain the intermediate 6n. This intermediate 6n was directly hydrogenolyzed in the crude state to give the product 2n in the form of a colorless oil, with a total yield of 37%. The product 2n was stored in its original state at −15 ° C.

EXAMPLE 15

2,3-Bis(2-menthoxyacetyl)-4,6-ethylidene-β-D-glucose 2o.

The procedure in Example 1 is repeated, but using 2-menthoxyacetyl chloride as a substitute for 2-phenoxyacetyl chloride, and for a reaction time of 16 h, in order to obtain the intermediate 6o. This intermediate 6o was directly hydrogenolyzed in the crude state to give the product 2o in the form of a colorless oil, with a total yield of 24%. The product 2o was stored in its original state at −15° C.

EXAMPLE 16

2,3-Bis(2,2-phenylidenedioxyacetyl)-4,6-ethylidene-β-D-glucose 2p.

The procedure in Example 1 is repeated, but using 2,2-phenylidenedioxyacetyl chloride as a substitute for 2-phenoxyacetyl chloride, and for a reaction time of 6 h, in order to obtain the intermediate 6p. This intermediate 6p was directly hydrogenolyzed in the crude state to give the product 2p in the form of a colorless oil, with a total yield of 15%. The product 2p was stored in its original state at −15° C.

EXAMPLE 17

2,3-Bis(2,2-naphthylidenedioxyacetyl)-4,6-ethylidene-β-D-glucose 2q.

The procedure in Example 1 is repeated, but using 2,2-naphthylidenedioxyacetyl chloride as a substitute for 2-phenoxyacetyl chloride, and for a reaction time of 9 h, in order to obtain the intermediate 6q. This intermediate 6q was directly hydrogenolyzed in the crude state to give the product 2q in the form of a colorless oil, with a total yield of 21%. The product 2q was stored in its original state at −15° C.

EXAMPLE 18

2,3-Bis(2-benzylthioacetyl)-4,6-ethylidene-β-D-glucose 2r.

The procedure in Example 1 is repeated, but using 2-benzylthioacetyl chloride as a substitute for 2-phenoxyacetyl chloride, and for a reaction time of 10 h, in order to obtain the intermediate 6r. This intermediate 6r was directly hydrogenolyzed in the crude state to give the product 2r in the form of a pale yellow resin, with a total yield of 34%. The product 2r was stored in its original state at −15° C.

EXAMPLE 19

2,3-Bis(2-phenylthioacetyl)-4,6-ethylidene-β-D-glucose 2s.

The procedure in Example 1 is repeated, but using 2-phenylthioacetyl chloride as a substitute for 2-phenoxyacetyl chloride, and for a reaction time of 10 h, in order to obtain the intermediate 6s. This intermediate 6s was directly hydrogenolyzed in the crude state to give the product 2s in the form of a yellow oil, with a total yield of 37%. The product 2s was stored in its original state at −15° C.

EXAMPLE 20

2,3-Difuroyl-4,6-ethylidene-β-D-glucose 2t.

The procedure in Example 1 is repeated, but using furoyl chloride as a substitute for 2-phenoxyacetyl chloride, and for a reaction time of 4 h, in order to obtain the intermediate 6t. This intermediate 6t was directly hydrogenolyzed in the crude state to give the product 2t in the form of a colorless oil, with a total yield of 41%. The product 2t was stored in its original state at −15° C.

Examples 21 to 40 illustrate the preparation of aglycones of the formula 3.

EXAMPLE 21

4'-(2-Phenoxyacetyl)-4'-demethylepipodophyllotoxin 3a.

To a mixture of dry dichloromethane (17 l) and anhydrous pyridine (657 ml, that is to say 1.3 equiv.), 4'-demethylepipodophyllotoxin (2.5 kg, that is to say 6.25 moles) is added. The reaction mixture was cooled to 0° C., then 2-phenoxyacetyl chloride (1122 ml, that is to say 1.3 equiv.) was added and the reaction was pursued at 20° C. for 2 h. After monitoring by thin layer chromatography, the mixture was washed with brine. The organic phase was dried over MgSO₄ and then concentrated under reduced pressure. The oil obtained was crystallized in ethyl acetate. 3 kg of a crystalline product were obtained (yield=90%). Structural analysis gave the following results: m.p.=110°-112° C.; $[\alpha]_D^{22} = -48°$ (c=1; CHCl₃); IR (Nujol) ($\nu$ max): 3550 (OH), 1770 (C=O), 1603, 1383 and 1338; ¹H NMR 90 MHz (CDCl₃) ($\delta$ ppm): 6.95 to 7.55 (5H, 2m, arom. H); 6.89 (1H, s, H-5); 6.53 (1H, s, H-8); 6.39 (2H, s, H-2', 6'); 5.99 (2H, s, O—CH₂—O); 4.95 (2H, s, benzylic H); 4.82 (1H, d, J₃=4 Hz, H-4); 4.64 (1H, d, J₁₋₂=5Hz, H-1); 4.33 (2H, m, H-11); 3.7 (6H, s, OCH₃); 3.29 (1H, dd, J₂₋₁=5 Hz, J₂₋₃=14.5 Hz, H-2) and 3.76 (2H, m, H-3, OH).

EXAMPLE 22

4'-(2-Naphthoxyacetyl)-4'-demethylepipodophyllotoxin 3b.

Following the procedure in Example 21, but using 2-naphthoxyacetyl chloride as a substitute for 2-phenoxyacetyl chloride, and a reaction time of 10 h 30, the product 3b was obtained in the form of an amorphous pale yellow powder (yield=38%).

EXAMPLE 23

4'-[2-(2-Methoxyphenoxy)acetyl]-4'-demethylepipodophyllotoxin 3c.

Following the procedure in Example 21, but using 2-(2-methoxyphenoxy) acetyl chloride as a substitute for 2-phenoxyacetyl chloride, and a reaction time of 4 h 30, the product 3c was obtained in the form of a translucent glass (yield=80%).

EXAMPLE 24

4'-[2-(4-Methoxyphenoxy)acetyl]-4'-demethylepipodophyllotoxin 3d.

Following the procedure in Example 21, but using 2-(4-methoxyphenoxy) acetyl chloride as a substitute for 2-phenoxyacetyl chloride, and a reaction time of 5 h, the product 3d was obtained in the form of a white powder (yield=82%).

EXAMPLE 25

4'-[2-(2-Nitrophenoxy)acetyl]-4'-demethylepipodophyllotoxin 3e.

Following the procedure in Example 21, but using 2-(2-nitrophenoxy) acetyl chloride as a substitute for 2-phenoxyacetyl chloride, and a reaction time of 2 h, the product 3e was obtained in the form of a light brown resin (yield=79%).

EXAMPLE 26

4'-[2-(4-Nitrophenoxy)acetyl]-4'-demethylepipodophyllotoxin 3f.

Following the procedure in Example 21, but using 2-(4-nitrophenoxy) acetyl chloride as a substitute for 2-phenoxyacetyl chloride, and a reaction time of 2 h 30, the product 3f was obtained in the form of an amorphous dark yellow powder (yield=73%).

EXAMPLE 27

4'-[2-(4-Chlorophenoxy)acetyl]-4'-demethylepipodophyllotoxin 3g.

Following the procedure in Example 21, but using 2-(4-chlorophenoxy) acetyl chloride as a substitute for 2-phenoxyacetyl chloride, and a reaction time of 3 h 30, the product 3g was obtained in the form of a pale yellow glass (yield=77%).

EXAMPLE 28

4'-[2-(2,4-Dichlorophenoxy)acetyl]-4'-demethylepipodophyllotoxin 3h.

Following the procedure in Example 21, but using 2-(2,4-dichlorophenoxy) acetyl chloride as a substitute for 2-phenoxyacetyl chloride, and a reaction time of 5 h, the product 3h was obtained in the form of a yellow powder (yield=67%).

EXAMPLE 29

4'-[2-(2,4,5-Trichlorophenoxy)acetyl]-4'-demethylepipodophyllotoxin 3i.

Following the procedure in Example 21, but using 2-(2,4,5-trichlorophenoxy) acetyl chloride as a substitute for 2-phenoxyacetyl chloride, and a reaction time of 8 h, the product 3i was obtained in the form of a white powder (yield=85%).

EXAMPLE 30

4'-[2-(2,4,6-Trichlorophenoxy)acetyl]-4'-demethylepipodophyllotoxin 3j.

Following the procedure in Example 21, but using 2-(2,4,6-trichlorophenoxy)acetyl chloride as a substitute for 2-phenoxyacetyl chloride, and a reaction time of 10 h, the product 3j was obtained in the form of an amorphous white powder (yield=81%).

EXAMPLE 31

4'-[2-(2-Fluorophenoxy)acetyl]-4'-demethylepipodophyllotoxin 3k.

Following the procedure in Example 21, but using 2-(2-fluorophenoxy) acetyl chloride as a substitute for 2-phenoxyacetyl chloride, and a reaction time of 1 h 30, the product 3k was obtained in the form of an amorphous white powder (yield=63%).

EXAMPLE 32

4'-(2-Methoxyacetyl)-4'-demethylepipodophyllotoxin 3l.

Following the procedure in Example 21, but using 2-methoxyacetyl chloride as a substitute for 2-phenoxyacetyl chloride, and a reaction time of 2 h, the product 3l was obtained in the form of a compound which crystallizes spontaneously on isolating (yield=84%); m.p.=200°-203° C.; $[\alpha]_D^{22} = -59°$(c=1, CHCl₃); IR (Nujol) (ν max); 3527 (OH), 1769 (C=O), 1600, 1484 and 1132.

EXAMPLE 33

4'-(2-Ethoxyacetyl)-4'-demethylepipodophyllotoxin 3m.

Following the procedure in Example 21, but using 2-ethoxyacetyl chloride as a substitute for 2-phenoxyacetyl chloride, and a reaction time of 2 h, the product 3m was obtained in the form of a white powder (yield=74%).

EXAMPLE 34

4'-(2-Benzoxyacetyl)-4'-demethylepipodophyllotoxin 3n.

Following the procedure in Example 21, but using 2-benzoxyacetyl chloride as a substitute for 2-phenoxyacetyl chloride, and a reaction time of 4 h, the product 3n was obtained in the form of white microcrystals (yield =82%); m.p.=209°–211° C.; $[α]_D^{22}$=−48°(c=1, CHCl$_3$); IR (Nujol) (ν max): 3550 (OH), 1769 (C=O), 1600, 1484 and 1132.

EXAMPLE 35

4'-(2-Menthoxyacetyl)-4'-demethylepipodophyllotoxin 3o.

Following the procedure in Example 21, but using 2-menthoxyacetyl chloride as a substitute for 2-phenoxyacetyl chloride, and a reaction time of 16 h, the product 3o was obtained in the form of a white powder (yield=33%).

EXAMPLE 36

4'-(2,2-Phenylidenedioxyacetyl)-4'-demethylepipodophyllotoxin 3p.

Following the procedure in Example 21, but using 2,2-phenylidenedioxyacetyl chloride as a substitute for 2-phenoxyacetyl chloride, and a reaction time of 4 h, the product 3p was obtained in the form of an amorphous yellow powder (yield=36%).

EXAMPLE 37

4'-(2,2-Naphthylidenedioxyacetyl)-4'-demethylepipodophyllotoxin 3q.

Following the procedure in Example 21, but using 2,2-naphthylidenedioxyacetyl chloride as a substitute for 2-phenoxyacetyl chloride, and a reaction time of 4 h, the product 3q was obtained in the form of an amorphous yellow powder (yield=30%).

EXAMPLE 38

4'-(2-Benzylthioacetyl)-4'-demethylepipodophyllotoxin 3r.

Following the procedure in Example 21, but using 2-benzylthioacetyl chloride as a substitute for 2-phenoxyacetyl chloride, and a reaction time of 4 h, the product 3r was obtained in the form of an amorphous white powder (yield=69% ).

EXAMPLE 39

4'-(2-Phenylthioacetyl)-4'-demethylepipodophyllotoxin 3s.

Following the procedure in Example 21, but using 2-phenylthioacetyl chloride as a substitute for 2-phenoxyacetyl chloride, and a reaction time of 4 h 30, the product 3s was obtained in the form of an amorphous white powder (yield=77% ).

EXAMPLE 40

4'-Furoyl-4'-demethylepipodophyllotoxin 3t.

Following the procedure in Example 21, but using furoyl chloride as a substitute for 2-phenoxyacetyl chloride, and a reaction time of 2 h, the product 3t was obtained in the form of an amorphous white powder (yield=83%).

Examples 41 to 60 illustrate the preparation of compounds 1, by reacting a glycosyl derivative 2 and an aglycone 3.

EXAMPLE 41

4'-Demethylepipodophyllotoxin 2″,3″,4'-tris(2-phenoxyacetyl)-4″,6″-ethylidene-β-D-glucopyranoside 1a.

4'-(2-phenoxyacetyl)-4'-demethylepipodophyllotoxin (3 kg, that is to say 5.62 moles) 3a obtained from Example 21 and 2,3-bis(2-phenoxyacetyl)-4,6-ethylidene-β-D-glucose 2a (3.2 kg, that is to say 6.74 moles or 1.2 equiv.), obtained from Example 1 are introduced into dry dichloromethane (18 l). After the temperature has stabilized at −18° C., boron trifluoride (1.73 l, that is to say 14.05 moles, i.e. 2.5 equiv.) was slowly added. The reaction was pursued at −18° C. for 2 h, then after monitoring by thin layer chromatography, pyridine (910 ml, that is to say 2 equiv.) was added. The solution was washed with water, then dried over MgSO$_4$ and concentrated under reduced pressure. The crude product was filtered on silica gel [70–200 ν; MeOH (2%)/CH$_2$Cl$_2$] and, after evaporation, 4.73 kg of an amorphous white powder were obtained. A sample was recrystallized for the purpose of an analytical study. The results are as follows:

Empirical formula: C$_{53}$H$_{50}$O$_{19}$
Molecular mass : 990
Yield : 85%
m.p. : 132°–134° C.
$[α]_D^{22}$=−67°(c=1; CHCl$_3$0

EXAMPLE 42

4'-Demethylepipodophyllotoxin 2″,3″, 4'-tris(2-naphthoxyacetyl)-4″,6″-ethylidene-β-D-glucopyranoside 1b.

The procedure in Example 41 was repeated, but using 2,3-bis(2-naphthoxyacetyl)-4,6-ethylidene-β-D-glucose 2b and 4'-(2-naphthoxyacetyl)-4'-demethylepipodophyllotoxin 3b, obtained from Examples 2 and 22, respectively, as substitutes for 2,3-bis(2-phenoxyacetyl)-4,6-ethylidene-β-D-glucose 2a and 4'-(2-phenoxyacetyl)-4'-demethylepipodophyllotoxin 3a, to obtain the desired product.

Empirical formula: C$_{65}$H$_{56}$O$_{19}$
Molecular mass : 1140
Yield : 58%
m.p. : 136°–139° C.
$[α]_D^{22}$=−60°(c=1; CHCl$_3$)

EXAMPLE 43

4'-Demethylepipodophyllotoxin 2″,3″,4'-tris[2-(2-methoxyphenoxy) acetyl]-4″,6″-ethylidene-β-D-glucopyranoside 1c.

The procedure in Example 41 was repeated, but using 2,3-bis [2-(2-methoxyphenoxy)acetyl]-4,6-ethylidene-β-

D-glucose 2c and 4'-[2-(2-methoxyphenoxy)acetyl]-4'-demethylepipodophyllotoxin 3c, obtained from Examples 3 and 23, respectively, as substitutes for 2,3-bis(2-phenoxyacetyl)-4,6-ethylidene-β-D-glucose 2a and 4'-(2phenoxyacetyl)-4' -demethylepipodophyllotoxin 3a, to obtain the desired product.

Empirical formula : $C_{56}H_{56}O_{22}$
Molecular mass : 1080
Yield : 75%
m.p. : 113°–115° C.
$[\alpha]_D^{22} = -52°(c=1; CHCl_3)$

EXAMPLE 44

4'-Demethylepipodophyllotoxin 2'',3'',4'-tris[2-(4-methoxyphenoxy) acetyl]-4'',6''-ethylidene-β-D-glucopyranoside 1d.

The procedure in Example 41 was repeated, but using 2,3-bis [2-(4-methoxyphenoxy)acetyl]-4,6-ethylidene-β-D-glucose 2d and 4'-[2-(4-methoxyphenoxy)acetyl]-4'-demethylepipodophyllotoxin 3d, obtained from Examples 4 and 24, respectively, as substitutes for 2,3-bis (-2-phenoxyacetyl)-4,6-ethylidene-β-D-glucose 2a and 4'-(2-phenoxyacetyl)-4'-demethylepipodophyllotoxin 3a, to obtain the desired product.

Empirical formula: $C_{56}H_{56}O_{22}$
Molecular mass : 1080
Yield : 73%
m.p. : 107°–109° C.
$[\alpha]_D^{22} = -61°(c=1; CHCl_3)$

EXAMPLE 45

4'-Demethylepipodophyllotoxin 2'',3'',4'-tris[2-(2-nitrophenoxy)acetyl]-4'',6''-ethylidene-β-D-glucopyranoside 1e.

The procedure in Example 41 was repeated, but using 2,3-bis[2-(2-nitrophenoxy)acetyl]-4,6-ethylidene-β-D-glucose 2e and 4'-[2-(2-nitrophenoxy)acetyl]-4'-demethylepipodophyllotoxin 3e, obtained from Examples 5 and 25, respectively, as substitutes for 2,3-bis(2-phenoxyacetyl)-4,6-ethylidene-β-D-glucose 2a and 4'-(2-phenoxyacetyl)-4'-demethylepipodophyllotoxin 3a, to obtain the desired product.

Empirical formula : $C_{53}H_{47}O_{25}N_3$
Molecular mass : 1125
Yield : 79%
m.p. : 135°–137° C.
$[\alpha]_D^{22} = -53°(c=1; CHCl_3)$

EXAMPLE 46

4'-Demethylepipodophyllotoxin 2'',3'',4'-tris[2-(4-nitrophenoxy)acetyl]-4'',6''-ethylidene-β-D-glucopyranoside 1f.

The procedure in Example 41 was repeated, but using 2,3-bis[2-(4-nitrophenoxy)acetyl]-4,6-ethylidene-β-D-glucose 2f and 4'-[2-(4-nitrophenoxy)acetyl]-4'-demethylepipodophyllotoxin 3f, obtained from Examples 6 and 26, respectively, as substitutes for 2,3-bis(2-phenoxyacetyl)-4,6-ethylidene-β-D-glucose 2a and 4'-(2-phenoxyacetyl)-4'-demethylepipodophyllotoxin 3a, to obtain the desired product.

Empirical formula : $C_{53}H_{47}O_{25}N_3$
Molecular mass : 1125
Yield : 82%
m.p. : 143°–145 ° C.
$[\alpha]_D^{22} = -72°(c=1; CHCl_3)$

EXAMPLE 47

4'-Demethylepipodophyllotoxin 2'',3'',4'-tris[2-(4-chlorophenoxy)acetyl]-4'',6''-ethylidene-β-D-glucopyranoside 1g.

The procedure in Example 41 was repeated, but using 2,3-bis[2-(4-chlorophenoxy)acetyl]-4,6-ethylidene-β-D-glucose 2g and 4'-[2-(4-chlorophenoxy)acetyl]-4'-demethylepipodophyllotoxin 3g, obtained from Examples 7 and 27, respectively, as substitutes for 2,3-bis(2-phenoxyacetyl)-4,6-ethylidene-62 -D-glucose 2a and 4'-(2-phenoxyacetyl)-4'-demethlepipodophyllotoxin 3a, to obtain the desired product.

Empirical formula : $C_{53}H_{47}O_{19}Cl_3$
Molecular mass : 1093.5
Yield : 79%
m.p. : 120°–123° C.
$[\alpha]_D^{22} = -63°(c=1; CHCl_3)$

EXAMPLE 48

4'-Demethylepipodophyllotoxin 2'',3'',4'-tris[2-(2,4-dichlorophenoxy)acetyl]-4'',6''-ethylidene-β-D-glucopyranoside 1h.

The procedure in Example 41 was repeated, but using 2,3-bis[2-(2,4-dichlorophenoxy)acetyl]-4,6-ethylidene-β-D-glucose 2h and 4'-[2-(2,4-dichlorophenoxy)acetyl]-4'-demethylepipodophyllotoxin 3h, obtained from Examples 8 and 28, respectively, as substitutes for 2,3-bis(2-phenoxyacetyl)-4,6-ethylidene-β-D-glucose 2a and 4'-(2-phenoxyacetyl)-4'-demethylepipodophyllotoxin 3a, to obtain the desired product.

Empirical formula : $C_{53}H_{44}O_{19}Cl_6$
Molecular mass : 1197
Yield : 85%
m.p. 115°–117° C.
$[\alpha]_D^{22} = -51°(c=1; CHCl_3)$

EXAMPLE 49

4'-Demethylepipodophyllotoxin 2'',3'',4'-tris[2-(2,4,5-trichlorophenoxy)acetyl]-4'',6''-ethylidene-β-D-glucopyranoside 1i.

The procedure in Example 41 was repeated, but using 2,3-bis[2-(2,4,5-trichlorophenoxy)acetyl]-4,6-ethylidene-β-D-glucose 2i and 4'-[2-(2,4,5-trichlorophenoxy)acetyl]-4'-demethylepipodophyllotoxin 3i, obtained from Examples 9 and 29, respectively, as substitutes for 2,3-bis(2-phenoxyacetyl)-4,6-ethylidene-β-D-glucose 2a and 4'-(2-phenoxyacetyl)-4'-demethylepipodophyllotoxin 3a, to obtain the desired product.

Empirical formula: $C_{53}H_{41}O_{19}Cl_9$
Molecular mass : 1300.5
Yield : 75%
m.p. : 126°–128° C.
$[\alpha]_D^{22} = -43°(c=1; CHCl_3)$

EXAMPLE 50

4'-Demethylepipodophyllotoxin 2'',3'',4'-tris[2-(2,4,6-trichlorophenoxy)acetyl]-4'',6''-ethylidene-β-D-glucopyranoside 1j.

The procedure in Example 41 was repeated, but using 2,3-bis[2-(2,4,6-trichlorophenoxy)acetyl]-4,6-ethylidene-β-D-glucose 2j and 4'-[2-(2,4,6-trichlorophenoxy)acetyl]-4'-demethylepipodophyllotoxin 3j, obtained from Examples 10 and 30, respectively, as substitutes for 2,3-bis(2-phenoxyacetyl)-4,6-ethylidene-β-D-glucose 2a and 4'-(2-phenoxyacetyl)-4'-demethylepipodophyllotoxin 3a, to obtain the desired product.

Empirical formula: $C_{53}H_{41}O_{19}Cl_9$
Molecular mass : 1300.5
Yield : 80%
m.p. : 120°–122° C.
$[\alpha]_D^{22} = -10°(c=1; CHCl_3)$

EXAMPLE 51

4'-Demethylepipodophyllotoxin
2″,3″,4'-tris[2-(2-fluorophenoxy)acetyl]-4″,6″-ethylidene-β-D-glucopyranoside 1k.

The procedure in Example 41 was repeated, but using 2,3-bis[2-(2-fluorophenoxy)acetyl]-4,6-ethylidene-β-D-glucose 2k and 4'-[2-(2-fluorophenoxy)acetyl]-4'-demethylepipodophyllotoxin 3k, obtained from Examples 11 and 31, respectively, as substitutes for 2,3-bis(2-phenoxyacetyl)-4,6-ethylidene-β-D-glucose 2a and 4'-(2-phenoxyacetyl)-4'-demethylepipodophyllotoxin 3a, to obtain the desired product.

Empirical formula : $C_{53}H_{47}O_{19}F_3$
Molecular mass : 1140
Yield 57%
m.p. : amorphous
$[\alpha]_D^{22} = -58°(c=1; CHCl_3)$

EXAMPLE 52

4'-Demethylepipodophyllotoxin
2″,3″,4'-tris(2-methoxyacetyl)-4″,6″-ethylidene-β-D-glucopyranoside 1l.

The procedure in Example 41 was repeated, but using 2,3-bis(2-methoxyacetyl)-4,6-ethylidene-β-D-glucose 2l and 4'-(2-methoxyacetyl)-4'-demethylepipodophyllotoxin 3l, obtained from Examples 12 and 32, respectively, as substitutes for 2,3-bis(2-phenoxyacetyl)-4,6-ethylidene-β-D-glucose 2a and 4'-(2-phenoxyacetyl)-4'-demethylepipodophyllotoxin 3a, to obtain the desired product.

Empirical formula : $C_{38}H_{44}O_{19}$
Molecular mass : 804
Yield : 82%
m.p. : 158–160
$[\alpha]_D^{22} = -67°(c=1; CHCl_3)$

EXAMPLE 53

4'-Demethylepipodophyllotoxin
2″,3″,4'-tris(2-ethoxyacetyl)-4″,6″-ethylidene-β-D-glucopyranoside 1m.

The procedure in Example 41 was repeated, but using 2,3-bis(2-ethoxyacetyl)-4,6-ethylidene-β-D-glucose 2m and 4'-(2-ethoxyacetyl)-4'-demethylepipodophyllotoxin 3m, obtained from Examples 13 and 33, respectively, as substitutes for 2,3-bis(2-phenoxyacetyl)-4,6-ethylidene-β-D-glucose 2a and 4'-(2-phenoxyacetyl)-4'-demethylepipodophyllotoxin 3a, to obtain the desired product.

Empirical formula: $C_{41}H_{50}O_{19}$
Molecular mass : 846
Yield : 71%
m.p. : 195–198
$[\alpha]_D^{22} = -64°(c=1; CHCl_3)$

EXAMPLE 54

4'-Demethylepipodophyllotoxin
2″,3″,4'-tris(2-benzoxyacetyl)-4″,6″-ethylidene-β-D-glucopyranoside 1n.

The procedure in Example 41 was repeated, but using 2,3-bis(2-benzoxyacetyl)-4,6-ethylidene-β-D-glucose 2n and 4'-(2-benzoxyacetyl)-4'-demethylepipodophyllotoxin 3n, obtained from Examples 14 and 34, respectively, as substitutes for 2,3-bis(2-phenoxyacetyl)-4,6-ethylidene-β-D-glucose 2a and 4'-(2-phenoxyacetyl)-4'-demethylepipodophyllotoxin 3a, to obtain the desired product.

Empirical formula : $C_{56}H_{56}O_{19}$
Molecular mass : 1032
Yield : 85%
m.p. : amorphous
$[\alpha]_D^{22} = -46°(c=1; CHCl_3)$

EXAMPLE 55

4'-Demethylepipodophyllotoxin
2″,3″,4'-tris(2-menthoxyacetyl)-4″,6″-ethylidene-β-D-glucopyranoside 1o.

The procedure in Example 41 was repeated, but using 2,3-bis(2-menthoxyacetyl)-4,6-ethylidene-β-D-glucose 2o and 4'-(2-menthoxyacetyl)-4'-demethylepipodophyllotoxin 3o, obtained from Examples 15 and 35, respectively, as substitutes for 2,3-bis(2-phenoxyacetyl)-4,6-ethylidene-β-D-glucose 2a and 4'-(2-phenoxyacetyl)-4'-demethylepipodophyllotoxin 3a, to obtain the desired product.

Empirical formula : $C_{65}H_{92}O_{19}$
Molecular mass : 1300.5
Yield : 68%
m.p. : amorphous
$[\alpha]_D^{22} = -97°(c=1; CHCl_3)$

EXAMPLE 56

4'-Demethylepipodophyllotoxin
2″,3″,4'-tris(2,2-phenylidenedioxyacetyl)-4″,6″-ethylidene-β-D-glucopyranoside 1p.

The procedure in Example 41 was repeated, but using 2,3-bis (2,2-phenylidenedioxyacetyl)-4,6-ethylidene-β-D-glucose 2p and 4'-(2,2-phenylidenedioxyacetyl)-4'-demethylepipodophyllotoxin 3p, obtained from Examples 16 and 36, respectively, as substitutes for 2,3-bis (2-phenoxyacetyl)-4,6-ethylidene-β-D-glucose 2a and 4'-(2-phenoxyacetyl)-4'-demethylepipodophyllotoxin 3a, to obtain the desired product.

Empirical formula: $C_{53}H_{44}O_{22}$
Molecular mass : 1032
Yield : 58%
m.p. : amorphous
$[\alpha]_D^{22} = -35°(c=1; CHCl_3)$

EXAMPLE 57 b 4'-Demethylepipodophyllotoxin
2″,3″,4'-tris(2,2-naphthylidenedioxyacetyl)-4″,6″-ethylidene-β-D-glucopyranoside 1q.

The procedure in Example 41 was repeated, but using 2,3-bis(2,2-naphthylidenedioxyacetyl)-4,6-ethylidene-β-D-glucose 2q and 4'-(2,2-naphthylidenedioxyacetyl)-4'-demethylepipodophyllotoxin 3q, obtained from Examples 17 and 37, respectively, as substitutes for 2,3-bis(2-phenoxyacetyl)-4,6-ethylidene-β-D-glucose 2a and 4'-

(2-phenoxyacetyl)-4'-demethylepipodophyllotoxin 3a, to obtain the desired product.
Empirical formula : C$_{65}$H$_{50}$O$_{22}$
Molecular mass : 1182
Yield : 64%
m.p. : 157≧159
$[\alpha]_D^{22}$ = −40°(c=1; CHCl$_3$)

EXAMPLE 58

4'-Demethylepipodophyllotoxin
2'',3'',4'-tris(2-benzylthioacetyl)-4'',6''-ethylidene-β-D-glucopyranoside 1r.

The procedure in Example 41 was repeated, but using 2,3-bis(2-benzylthioacetyl)-4,6-ethylidene-β-D-glucose 2r and 4'-(2-benzylthioacetyl)-4'-demethylepipodophyllotoxin 3r, obtained from Examples 18 and 38, respectively, as substitutes for 2,3-bis(2-phenoxyacetyl)-4,6-ethylidene-β-D-glucose 2a and 4'-(2-phenoxyacetyl)-4'-demethylepipodophyllotoxin 3a, to obtain the desired product.
Empirical formula: C$_{56}$H$_{56}$O$_{16}$S$_3$
Molecular mass : 1080
Yield : 49%
m.p. : amorphous
$[\alpha]_D^{22}$ = −48°(c=1; CHCl$_3$)

EXAMPLE 59

4'-Demethylepipodophyllotoxin
2'',3'',4'-tris(2-phenylthioacetyl)-4'',6''-ethylidene-β-D-glucopyranoside 1s.

The procedure in Example 41 was repeated, but using 2,3-bis(2-phenylthioacetyl)-4,6-ethylidene-β-D-glucose 2s and 4'-(2-phenylthioacetyl)-4'-demethylepipodophyllotoxin 3s, obtained from Examples 19 and 39, respectively, as substitutes for 2,3-bis(2-phenoxyacetyl)-4,6-ethylidene-β-D-glucose 2a, and 4'-(2-phenoxyacetyl)-4'-demethylepipodophyllotoxin 3a, to obtain the desired product.
Empirical formula : C$_{53}$H$_{50}$O$_{16}$S$_3$
Molecular mass : 1038
Yield : 82%
m.p. : amorphous
$[\alpha]_D^{22}$ = −60°(c=1; CHCl$_3$)

EXAMPLE 60

4'-Demethylepipodophyllotoxin
2'',3'',4'-trifuroyl-4'',6''-ethylidene-β-D-glucopyranoside 1t.

The procedure in Example 41 was repeated, but using 2,3-difuroyl-4,6-ethylidene-β-D-glucose 2t and 4'-furoyl-4'-dimethylepipodophyllotoxin 3t, obtained from Examples 20 and 30, respectively, as substitutes for 2,3-bis(2-phenoxyacetyl)-4,6-ethylidene-β-D-glucose 2a and 4'-(1-phenoxyacetyl)-4'-demethylepipodophyllotoxin 3a, to obtain the desired product.
Empirical formula: C$_{44}$H$_{38}$O$_{19}$
Molecular mass : 870
Yield : 89%
m.p. : 278–280
$[\alpha]_D^{22}$ = −15°(c=1; CHCl$_3$)

The following examples illustrate the use of the compounds 1 for preparing 4'-demethylepipodophyllotoxin 4,6-ethylidene-β-D-glucopyranoside 1'.

EXAMPLE 61

Preparation of 1' from 4'-demethylepipodophyllotoxin 2'',3'',4'-tris(2-phenoxyacetyl)-4'',6''-ethylidene-β-D-glucopyranoside 1a.

4'-demethylepipodophyllotoxin 2'',3'',4'-tris(2-phenoxyacetyl)-4'',6''-ethylidene-β-D-glucopyranoside 1a obtained from Example 41 (2.2 kg, that is to say 2.22 moles) was suspended in methanol (25 l) containing added tetrahydrofuran (2.5 l). Zinc acetate (1.1 kg) was added, then the reaction mixture was heated under reflux for 5 h. After monitoring by thin layer chromatography, the solution was concentrated and the concentrate introduced into dichloromethane (25 l) containing an added mixture of 6% acetic acid in methanol (3.5 l). The solution was washed with water, dried over MgSO$_4$, then evaporated under reduced pressure, until a thick oil was obtained which was subjected in its original state to chromatography on silica gel [20–45 μm; MeOH (2 to 5%)/CH$_2$Cl$_2$]. M=979 g; yield=75%; m.p.=257°–266° C. (CH$_2$Cl$_2$/Et$_2$O; cross-twinned prisms); $[\alpha]_D^{22}$ = −103°(c=0.6; CHCl$_3$).

EXAMPLE 62

Preparation of 1' from 4'-demethylepipodophyllotoxin 2'',3'',4'-tris(2-naphthoxyacetyl)-4'',6''-ethylidene-β-D-glucopyranoside 1b.

The procedure in Example 61 was repeated, but using the triester mentioned in the title as a substitute for 4'-demethylepipodophyllotoxin 2'',3'',4'-tris(2-phenoxyacetyl)-4'',6''-ethylidene-β-D-glucopyranoside 1a. The reaction was judged to be complete by thin layer chromatography after 6 h. The compound obtained is in all respects identical, on the one hand, to the one obtained in Example 61, and on the other, to a reference sample, with a yield of 70% of crystallized product.

EXAMPLE 63

Preparation of 1' from 4'-demethylepipodophyllotoxin 2'',3'',4'-tris[2-(2-metholyphenoly)acetyl]-4'',6''-ethylidene-β-D-glucopyranoside 1c.

The procedure in Example 61 was repeated, but using the triester mentioned in the title as a substitute for 4'-demethylepipodophyllotoxin 2'',3'',4'-tris(2-phenoxyacetyl)-4'',6''-ethylidene-β-D-glucopyranoside 1a. The reaction was judged to be complete by thin layer chromatography after 5 h. The compound obtained is in all respects identical, on the one hand, to the one obtained in Example 61, and on the other, to a reference sample, with a yield of 78% of crystallized product.

EXAMPLE 64

Preparation of 1' from 4'-demethylepipodophyllotoxin 2'',3'',4'-tris[2-(4-methoxyphenoxy)acetyl]-4'',6''-ethylidene-β-D-glucopyranoside 1d.

The procedure in Example 61 was repeated, but using the triester mentioned in the title as a substitute for 4'-demethylepipodophyllotoxin 2'',3'',4'-tris(2-phenoxyacetyl)-4'',6''-ethylidene-β-D-glucopyranoside 1a. The reaction was Judged to be complete by thin layer chromatography after 5 h. The compound obtained is in all respects identical, on the one hand, to the one obtained in Example 61, and on the other, to a reference sample, with a yield of 85% of crystallized product.

EXAMPLE 65

Preparation of 1' from 4'-demethylepipodophyllotoxin 2",3",4'-tris[2-(2-nitrophenoxy)acetyl]-4",6"-ethylidene-β-D-glucopyranoside 1e.

The procedure in Example 61 was repeated, but using the triester mentioned in the title as a substitute for 4'-demethylepipodophyllotoxin 2",3",4'-tris(2-phenoxyacetyl)-4",6"-ethylidene-β-D-glucopyranoside 1a. The reaction was judged to be complete by thin layer chromatography after 4 h. The compound obtained is in every respect identical, on the one hand, to the one obtained in Example 61, and on the other, to a reference sample, with a yield of 80% of crystallized product.

EXAMPLE 66

Preparation of 1' from 4'-demethylepipodophyllotoxin 2",3",4'-tris [2-( 4-nitrophenoxy)acetyl ]-4",6"-ethylidene-β-D-glucopyranoside 1f.

The procedure in Example 61 was repeated, but using the triester mentioned in the title as a substitute for 4'-demethylepipodophyllotoxin 2",3",4'-tris(2-phenoxyacetyl)-4",6"-ethylidene-β-D-glucopyranoside 1a. The reaction was judged to be complete by thin layer chromatography after 4 h. The compound obtained is in every respect identical, on the one hand, to the one obtained in Example 61, and on the other, to a reference sample, with a yield of 87% of crystallized product.

EXAMPLE 67

Preparation of 1' from 4'-demethylepipodophyllotoxin 2",3",4'-tris[2-(4-chlorophenoxy)acetyl]-4",6"-ethylidene-β-D-glucopyranoside 1g.

The procedure in Example 61 was repeated, but using the triester mentioned in the title as a substitute for 4'-demethylepipodophyllotoxin 2",3",4'-tris(2-phenoxyacetyl)-4",6"-ethylidene-β-D-glucopyranoside 1a. The reaction was Judged to be complete by thin layer chromatography after 4 h. The compound obtained is in every respect identical, on the one hand, to the one obtained in Example 61, and on the other, to a reference sample, with a yield of 82% of crystallized product.

EXAMPLE 68

Preparation of 1' from 4'-demethylepipodophyllotoxin 2",3",4'-tris[2-(2,4-dichlorophenoxy)acetyl]-4",6"-ethylidene-β-D-glucopyranoside 1h.

The procedure in Example 61 was repeated, but using the triester mentioned in the title as a substitute for 4'-demethylepipodophyllotoxin (2,"3",4'-tris(2,4-dichlorophenoxy)acetyl]-4",6"-ethylidene-β-D-glucopyranoside 1a. The reaction was Judged to be complete by thin layer chromatography after 4 h. The compound obtained is in every respect identical, on the one hand, to the one obtained in Example 61, and on the other, to a reference sample, with a yield of 82% of crystallized product.

EXAMPLE 69

Preparation of 1' from 4'-demethylepipodophyllotoxin 2",3",4'-tris[2-(2,4,5-trichlorophenoly)acetyl]-4",6"-ethylidene-β-D-glucopyranoside 1i.

The procedure in Example 61 was repeated, but using the triester mentioned in the title as a substitute for 4'-demethylepipodophyllotoxin 2",3",4'-tris(2-phenoxyacetyl)-4",6"-ethylidene-β-D-glucopyranoside 1a. The reaction was judged to be complete by thin layer chromatography after 4 h. The compound obtained is in every respect identical, on the one hand, to the one obtained in Example 61, and on the other, to a reference sample, with a yield of 85% of crystallized product.

EXAMPLE 70

Preparation of 1' from 4'-demethylepipodophyllotoxin 2",3",4'-tris[2-(2,4,6-trichlorophenoly)acetyl]-4",6"-ethylidene-β-D-glucopyranoside 1j.

The procedure in Example 61 was repeated, but using the triester mentioned in the title as a substitute for 4'-demethylepipodophyllotoxin 2",3",4'-tris(2-phenoxyacetyl)-4",6"-ethylidene-β-D-glucopyranoside 1a. The reaction was judged to be complete by thin layer chromatography after 4 h. The compound obtained is in every respect identical, on the one hand, to the one obtained in Example 61, and on the other, to a reference sample, with a yield of 82% of crystallized product.

EXAMPLE 71

Preparation of 1' from 4'-demethylepipodophyllotoxin 2",3",4'-tris[2-(2-fluorophenoxy)acetyl]-4",6"-ethylidene-β-D-glucopyranoside 1k.

The procedure in Example 61 was repeated, but using the triester mentioned in the title as a substitute for 4'-demethylepipodophyllotoxin 2",3",4'-tris(2-phenoxyacetyl)-4",6"-ethylidene-β-D-glucopyranoside 1a. The reaction was judged to be complete by thin layer chromatography after 4 h. The compound obtained is in every respect identical, on the one hand, to the one obtained in Example 61, and on the other, to a reference sample, with a yield of 91% of crystallized product.

EXAMPLE 72

Preparation of 1' from 4'-demethylepipodophyllotoxin 2",3",4'-tris(2-methoxyacetyl)-4",6-ethylidene-β-D-glucopyranoside 1l.

The procedure in Example 61 was repeated, but using the triester mentioned in the title as a substitute for 4'-demethylepipodophyllotoxin 2",3",4'-tris(2-phenoxyacetyl)-4",6"-ethylidene-β-D-glucopyranoside 1a. The reaction was judged to be complete by thin layer chromatography after 4 h. The compound obtained is in every respect identical, on the one hand, to the one obtained in Example 61, and on the other, to a reference sample, with a yield of 70% of crystallized product.

EXAMPLE 73

Preparation of 1' from 4'-demethylepipodophyllotoxin 2",3",4'-tris(2-ethoxyacetyl)-4",6"-ethylidene-β-D-glucopyranoside 1m.

The procedure in Example 61 was repeated, but using the triester mentioned in the title as a substitute for 4'-demethylepipodophyllotoxin 2",3",4'-tris(2-phenoxyacetyl)-4",6"-ethylidene-β-D-glucopyranoside 1a. The reaction was judged to be complete by thin layer chromatography after 4 h. The compound obtained is in every respect identical, on the one hand, to the one obtained in Example 61, and on the other, to a reference sample, with a yield of 61% of crystallized product.

EXAMPLE 74

Preparation of 1' from 4'-demethylepipodophyllotoxin 2'',3'',4'-tris(2-benzoxyacetyl)-4'',6''-ethylidene-β-D-glucopyranoside 1n.

The procedure in Example 61 was repeated, but using the triester mentioned in the title as a substitute for 4'-demethylepipodophyllotoxin 2'',3'',4'-tris(2-phenoxyacetyl)-4'',6''-ethylidene-β-D-glucopyranoside 1a. The reaction was judged to be complete by thin layer chromatography after 4 h. The compound obtained is in every respect identical, on the one hand, to the one obtained in Example 61, and on the other, to a reference sample, with a yield of 86% of crystallized product.

EXAMPLE 75

Preparation of 1 ' from 4 '-demethylepipodophyllotoxin 2'',3'',4'-tris(2-menthoxyacetyl)-4'',6''-ethylidene-β-D-glucopyranoside 1a.

The procedure in Example 61 was repeated, but using the triester mentioned in the title as a substitute for 4'-demethylepipodophyllotoxin 2'',3'',4'-tris(2-phenoxyacetyl)-4'',6''-ethylidene-β-D-glucopyranoside 1a. The reaction was judged to be complete by thin layer chromatography after 4 h. The compound obtained is in every respect identical, on the one hand, to the one obtained in Example 61, and on the other, to a reference sample, with a yield of 15% of crystallized product.

EXAMPLE 76

Preparation of 1' from 4'-demethylepipodophyllotoxin 2'',3'',4'-tris(2,2-phenylidenedioxyacetyl)-4'',6''-ethylidene-β-D-glucopyranoside 1p.

The procedure in Example 61 was repeated, but using the triester mentioned in the title as a substitute for 4'-demethylepipodophyllotoxin 2'',3'',4'-tris(2-phenoxyacetyl)-4'',6''-ethylidene-β-D-glucopyranoside 1a. The reaction was judged to be complete by thin layer chromatography after 1 h. The compound obtained is in every respect identical, on the one hand, to the one obtained in Example 61, and on the other, to a reference sample, with a yield of 79% of crystallized product.

EXAMPLE 77

Preparation of 1 ' from 4 '-demethylepipodophyllotoxin 2'',3'',4'-tris(2,2-naphthylidenedioxyacetyl)-4'',6''-ethylidene-β-D-glucopyranoside 1q.

The procedure in Example 61 was repeated, but using the triester mentioned in the title as a substitute for 4'-demethylepipodophyllotoxin 2'',3'',4'-tris(2-phenoxyacetyl)-4'',6''-ethylidene-β-D-glucopyranoside 1a. The reaction was judged to be complete by thin layer chromatography after 1 h. The compound obtained is in every respect identical, on the one hand, to the one obtained in Example 61, and on the other, to a reference sample, with a yield of 90% of crystallized product.

EXAMPLE 78

Preparation of 1' from 4'-demethylepipodophyllotoxin 2'',3'',4'-tris(2-benzylthioacetyl)-4'',6''-ethylidene-β-D-glucopyranoside 1r.

The procedure in Example 61 was repeated, but using the triester mentioned in the title as a substitute for 4'-demethylepipodophyllotoxin 2'',3'',4'-tris(2-phenoxyacetyl)-4'',6''-ethylidene-β-D-glucopyranoside 1a. The reaction was judged to be complete by thin layer chromatography after 6 h. The compound obtained is in every respect identical, on the one hand, to the one obtained in Example 61, and on the other, to a reference sample, with a yield of 64% of crystallized product.

EXAMPLE 79

Preparation of 1' from 4'-demethylepipodophyllotoxin 2'',3'',4'-tris(2-phenylthioacetyl)-4'',6''-ethylidene-β-D-glucopyranoside 1s.

The procedure in Example 61 was repeated, but using the triester mentioned in the title as a substitute for 4'-demethylepipodophyllotoxin 2'',3'',4'-tris(2-phenoxyacetyl)-4'',6''-ethylidene-β-D-glucopyranoside 1a. The reaction was Judged to be complete by thin layer chromatography after 7 h. The compound obtained is in every respect identical, on the one hand, to the one obtained in Example 61, and on the other, to a reference sample, with a yield of 55% of crystallized product.

EXAMPLE 80

Preparation of 1' from 4'-demethylepipodophyllotoxin 2'',3'',4'-trifuroyl-4'',6''-ethylidene-β-D-glucopyranoside 1t.

The procedure in Example 61 was repeated, but using the triester mentioned in the title as a substitute for 4'-demethylepipodophyllotoxin 2'',3'',4'-tris(2-phenoxyacetyl)-4'',6''-ethylidene-β-D-glucopyranoside 1a. The reaction was judged to be complete by thin layer chromatography after 24 h. The compound obtained is in every respect identical, on the one hand, to the one obtained in Example 61, and on the other, to a reference sample, with a yield of 22% of crystallized product.

what is claimed is:

1. A process for the preparation of compounds of the formula 1

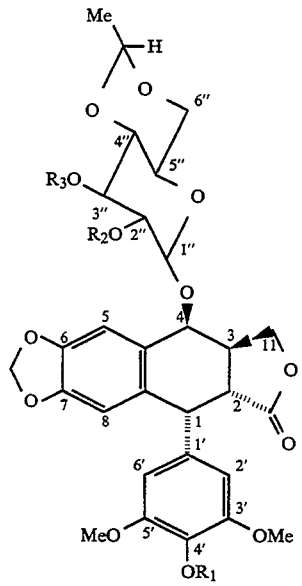

in which $R_1$, $R_2$, and $R_3$, are identical or different, represent acyl radicals in which the carbon in α of the carbonyl function bears at least one heteroatom selected from the group consisting of O and S, which comprises the following stages:

1) The preparation of β glycosyl derivative of the formula 2

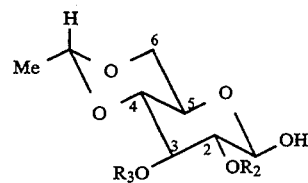

2

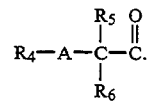

(4a)

in which $R_2$ and $R_3$ have the meaning given above, by reacting at least one acid chloride $R_2Cl$ or $R_3Cl$ in which the carbon in α of the carbonyl function bears at least one heteroatom selected from the group consisting of O and S with β glycosyl derivative of the formula 2',

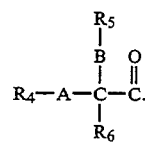

(4b)

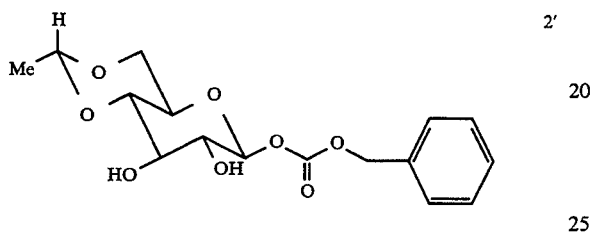

2'

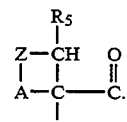

(4c)

followed by hydrogenolysis at atmospheric pressure of the intermediate compound 6 obtained, catalyzed by palladized carbon;

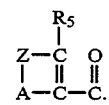

(4d)

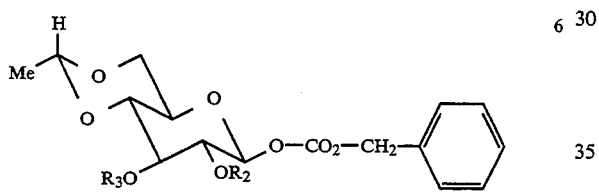

6

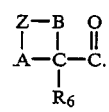

(4e)

2) The preparation of an aglycone of the formula 3,

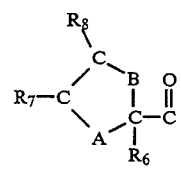

(4f)

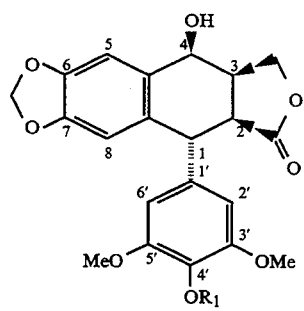

3

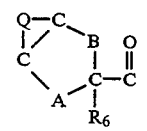

(4g)

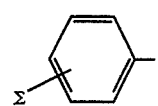

(4h)

in which $R_1$ has the meaning given above, by reacting 4'-demethylepipodophyllotoxin with an acid chloride $R_1Cl$ in which the carbon in α of the carbonyl function bears at least one heteroatom selected from the group consisting of O and S, the reaction being carried out in a neutral medium; the order in which the stages 1) and 2) are carried out being unimportant;

3) The coupling of a crude derivative 2 prepared from step 1 with an aglycone 3 in the presence of a Lewis acid in solution in a chlorine-containing hydrocarbon.

2. A process as claimed in claim 1, wherein the acid chlorides, which are identical or different, are selected from the group consisting of the acid chlorides whose acyl radical $R_1$, $R_2$ or $R_3$ is of the formulae 4a to 4h below:

in which
A and B, which are identical or different, each represent a divalent heteroatom of oxygen or sulfur,
$R_4$, $R_5$, $R_6$, $R_7$ and $R_8$, which are identical or different, each represent either a hydrogen atom or an alkyl radical with 1 to 8 carbon atoms which is saturated, monounsaturated or polyunsaturated, linear or branched, or an alkyl radical chosen from among the following groups: Ar—$(CH_2)_n$—(where n is an integer equal to 1 or 2, and Ar is a benzene, a naphthalene or an anthracene), $Ar_2CH$— (where Ar is a benzene or a naphthalene), or an aromatic ring selected from the group consisting of the formulae 5a to 5c below (5a)

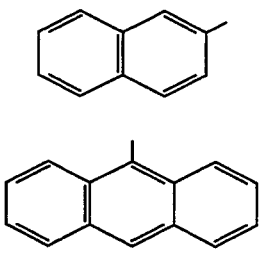 (5b)

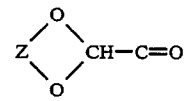 (5c)

where Σ represents a set of 1 to 4 identical or different substituents selected from the group consisting of the following groups or atoms: OMe, OEt, F, Cl, Br, I and NO$_2$ Z and Q, which are identical or different, each represent a divalent group selected from the group consisting of —(CH$_2$)$_n$—, —CH(CH$_3$)—CH$_2$—, —CH$_2$—CH(CH$_3$)—, —CH(CH$_3$)—CH(CH$_3$)—, —CH(C$_2$H$_5$)—CH$_2$—, —CH$_2$.CH(C$_2$—H$_5$) —, —CH=CH—, —CH=C(CH$_3$)—, —C(CH$_3$)=CH—, —CH=CH—(CH$_2$)$_m$ and —CH=CH—CH=CH, n being an integer from 1 to 4 inclusive and m an integer equal to 1 or 2, a 1,2-phenylene, 2,3-naphthylene or 2,3-anthrylene radical or a tetravalent group of the following formula:

=C(R$_9$)—CR$_{10}$=CR$_{11}$—CR$_{12}$=,

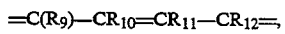

where R$_9$, R$_{10}$, R$_{11}$ and R$_{12}$ are alkyl radicals having from 1 to 6 carbon atoms or heteroatoms of oxygen, sulfur, halogens (F, Cl, Br, I), or nitrogen.

3. A process as claimed in one of claims 1 or 2, wherein at least one of the acyl radicals is an aryloxyacetyl radical R$_4$—O—CH$_2$—C=O, R$_4$ selected from the group consisting of phenoxy, naphthoxy, anthroxy and phenanthroxy rings, optionally having from 1 to 4 substituents selected from the group consisting of OMe, OEt, F, Cl, Br, I and NO$_2$.

4. A process as claimed in one of claims 1 or 2, wherein at least one of the acyl radicals is the alkoxyacetyl radical R$_4$—OCH$_2$—C=O, R$_4$ selected from the group consisting of the methyl, ethyl, benzyl and menthyl radicals.

5. A process as claimed in any one of claims 1 to 2, wherein at least one of the acyl radicals is the arylidenedioxyantyl radical $$Z\diagdown\begin{matrix}O\\ \\O\end{matrix}\diagup CH—C=O$$

, Z selected from the group consisting of phenylene, naphthylene, anthrylene and phenanthrylene.

6. A process as claimed in any one of claims 1 or 2, wherein at least one of the acyl radicals is the alkylthioacetyl radical R$_4$—S—CH$_2$—C=O, R$_4$ selected from the group consisting of the methyl, ethyl and benzyl radicals.

7. A process as claimed in any one of the claims 1 to 2, wherein at least one of the acyl radicals is the arylthioacetyl radical R$_4$—S—CH$_2$—C=O, R$_4$ selected from the group consisting of the phenyl, naphthyl and anthracenyl radicals.

8. A process as claimed in any one of claims 1 or 2, wherein at least one of the acyl radicals is selected from the group consisting of 2-furoyl and 2-thenoyl radicals.

* * * * *